United States Patent
Eppihimer et al.

(10) Patent No.: US 10,716,671 B2
(45) Date of Patent: Jul. 21, 2020

(54) PROSTHETIC HEART VALVE COMPOSED OF COMPOSITE FIBERS

(71) Applicant: Boston Scientific SciMed, Inc., Maple Grove, MN (US)

(72) Inventors: Michael Eppihimer, Franklin, MA (US); Peter G. Edelman, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/193,794

(22) Filed: Jun. 27, 2016

(65) Prior Publication Data

US 2017/0000610 A1  Jan. 5, 2017

Related U.S. Application Data

(60) Provisional application No. 62/188,201, filed on Jul. 2, 2015.

(51) Int. Cl.
 *A61F 2/24* (2006.01)

(52) U.S. Cl.
 CPC .......... *A61F 2/2469* (2013.01); *A61F 2/2409* (2013.01); *A61F 2/2412* (2013.01); *A61F 2230/0069* (2013.01); *A61F 2230/0091* (2013.01); *A61F 2240/001* (2013.01); *A61F 2250/0018* (2013.01)

(58) Field of Classification Search
 CPC .................................................... A61F 2/2412
 USPC ....................................................... 428/377
 See application file for complete search history.

(56) References Cited

U.S. PATENT DOCUMENTS

| 4,016,714 A | * | 4/1977 | Crandall | A63B 51/02 57/234 |
|---|---|---|---|---|
| 4,340,091 A | | 7/1982 | Davis et al. | |
| 4,753,652 A | | 6/1988 | Langer et al. | |
| 5,296,292 A | * | 3/1994 | Butters | A01K 91/12 428/373 |
| 5,476,507 A | | 12/1995 | Wakabayashi et al. | |
| 5,674,286 A | | 10/1997 | D'Alessio et al. | |
| 5,679,299 A | | 10/1997 | Gilbert et al. | |
| 5,688,597 A | * | 11/1997 | Kohno | B29C 70/20 152/451 |
| 5,740,051 A | | 4/1998 | Sanders, Jr. et al. | |

(Continued)

FOREIGN PATENT DOCUMENTS

| CN | 1449266 | 10/2003 |
|---|---|---|
| CN | 1874799 | 12/2006 |

(Continued)

OTHER PUBLICATIONS

"International Search Report and Written Opinion," for PCT application No. PCT/US2016/050691 dated Dec. 19, 2016 (14 pages).

(Continued)

*Primary Examiner* — Jacqueline Woznicki
(74) *Attorney, Agent, or Firm* — Pauly, DeVries Smith & Deffner LLC (57) ABSTRACT

A prosthetic heart leaflet includes a fiber-reinforced structure including a plurality of composite fibers. Each composite fiber includes a core fiber and a sheathing fiber disposed about the core fiber, wherein the core fiber or the sheathing fiber has a curvilinear shape.

10 Claims, 8 Drawing Sheets

(56) References Cited

U.S. PATENT DOCUMENTS

| | | | |
|---|---|---|---|
| 5,843,158 A | 12/1998 | Lenker et al. | |
| 6,165,215 A | 12/2000 | Rottenberg et al. | |
| 6,726,715 B2 | 4/2004 | Sutherland | |
| 6,953,332 B1 | 10/2005 | Kurk et al. | |
| 7,335,264 B2 | 2/2008 | Austin et al. | |
| 7,517,353 B2 | 4/2009 | Weber | |
| 7,521,296 B2 | 4/2009 | Wood et al. | |
| 7,615,335 B2 | 11/2009 | Shelnut et al. | |
| 7,786,670 B2 | 8/2010 | Veres et al. | |
| 7,988,900 B2 | 8/2011 | Beith et al. | |
| 8,324,290 B2 | 12/2012 | Desai et al. | |
| 8,361,144 B2 | 1/2013 | Fish et al. | |
| 8,590,747 B2 | 11/2013 | Keller et al. | |
| 8,845,580 B2 | 9/2014 | Gellman et al. | |
| 8,864,816 B2 | 10/2014 | Flanagan et al. | |
| 8,945,212 B2 | 2/2015 | Bruchman et al. | |
| 8,975,372 B2 | 3/2015 | Ju et al. | |
| 9,056,006 B2 | 6/2015 | Edelman et al. | |
| 9,074,318 B2 * | 7/2015 | Chou | D07B 1/142 |
| 9,255,929 B2 | 2/2016 | Jiang et al. | |
| 9,481,949 B2 | 11/2016 | Zhang et al. | |
| 9,554,900 B2 | 1/2017 | Bruchman et al. | |
| 9,737,400 B2 | 8/2017 | Fish et al. | |
| 9,814,572 B2 | 11/2017 | Edelman et al. | |
| 9,944,529 B2 | 4/2018 | Zhang et al. | |
| 9,987,130 B2 | 6/2018 | Weber | |
| 10,195,023 B2 | 2/2019 | Wrobel | |
| 10,299,915 B2 | 5/2019 | Edelman et al. | |
| 10,314,696 B2 | 6/2019 | Wulfman et al. | |
| 10,368,982 B2 | 8/2019 | Weber et al. | |
| 10,413,403 B2 | 9/2019 | Boden et al. | |
| 10,426,609 B2 | 10/2019 | Edelman et al. | |
| 10,433,955 B2 | 10/2019 | Edelman et al. | |
| 2001/0025196 A1 | 9/2001 | Chinn et al. | |
| 2002/0082689 A1 | 6/2002 | Chinn et al. | |
| 2003/0055496 A1 | 3/2003 | Cai et al. | |
| 2003/0078652 A1* | 4/2003 | Sutherland | A61F 2/2412 623/2.12 |
| 2003/0097175 A1 | 5/2003 | O'connor et al. | |
| 2003/0171802 A1 | 9/2003 | Wilder et al. | |
| 2003/0183982 A1 | 10/2003 | Jansen et al. | |
| 2004/0015233 A1 | 1/2004 | Jansen et al. | |
| 2004/0022939 A1 | 2/2004 | Kim et al. | |
| 2005/0228486 A1* | 10/2005 | Case | A61F 2/07 623/1.24 |
| 2006/0190074 A1 | 8/2006 | Hill et al. | |
| 2007/0118210 A1 | 5/2007 | Pinchuk et al. | |
| 2007/0144124 A1 | 6/2007 | Schewe et al. | |
| 2007/0232169 A1 | 10/2007 | Strickler et al. | |
| 2007/0254005 A1 | 11/2007 | Pathak et al. | |
| 2008/0045420 A1 | 2/2008 | Karagianni et al. | |
| 2009/0041978 A1 | 2/2009 | Sogard et al. | |
| 2009/0054969 A1* | 2/2009 | Salahieh | A61F 2/2418 623/1.26 |
| 2009/0117334 A1 | 5/2009 | Sogard et al. | |
| 2009/0149673 A1 | 6/2009 | Zhang et al. | |
| 2009/0155335 A1 | 6/2009 | Oshaughnessey et al. | |
| 2009/0324679 A1 | 12/2009 | Ippoliti et al. | |
| 2010/0023104 A1 | 1/2010 | Desai et al. | |
| 2010/0179298 A1 | 7/2010 | Faust et al. | |
| 2010/0249922 A1 | 9/2010 | Li et al. | |
| 2011/0022160 A1 | 1/2011 | Flanagan et al. | |
| 2011/0208299 A1 | 8/2011 | Marissen et al. | |
| 2011/0305898 A1 | 12/2011 | Zhang et al. | |
| 2012/0101567 A1 | 4/2012 | Jansen | |
| 2012/0258313 A1 | 10/2012 | Wen et al. | |
| 2012/0290082 A1 | 11/2012 | Quint et al. | |
| 2013/0150957 A1 | 6/2013 | Weber et al. | |
| 2013/0211508 A1 | 8/2013 | Lane et al. | |
| 2013/0274874 A1 | 10/2013 | Hammer et al. | |
| 2014/0005771 A1 | 1/2014 | Braido et al. | |
| 2014/0005772 A1 | 1/2014 | Edelman et al. | |
| 2014/0018440 A1 | 1/2014 | Boden et al. | |
| 2014/0088716 A1 | 3/2014 | Zubok et al. | |
| 2014/0163671 A1 | 6/2014 | Bruchman et al. | |
| 2014/0180402 A1 | 6/2014 | Bruchman et al. | |
| 2014/0322512 A1* | 10/2014 | Pham | D01F 8/16 428/220 |
| 2015/0005869 A1 | 1/2015 | Soletti et al. | |
| 2015/0182332 A1 | 7/2015 | Edelman et al. | |
| 2015/0265392 A1 | 9/2015 | Flanagan et al. | |
| 2016/0296322 A1 | 10/2016 | Edelman | |
| 2016/0296323 A1* | 10/2016 | Wulfman | A61L 27/34 |
| 2016/0296325 A1* | 10/2016 | Edelman | A61F 2/2409 |
| 2017/0014227 A1 | 1/2017 | Boden et al. | |
| 2017/0071729 A1 | 3/2017 | Wrobel | |
| 2017/0156854 A1 | 6/2017 | Hammer | |
| 2017/0231758 A1 | 8/2017 | Bruchman et al. | |
| 2017/0266350 A1 | 9/2017 | Jiang et al. | |
| 2017/0333185 A1 | 11/2017 | Weber et al. | |
| 2018/0049869 A1 | 2/2018 | Edelman et al. | |
| 2018/0303972 A1 | 10/2018 | Delaney, Jr. et al. | |
| 2019/0262131 A1 | 8/2019 | Wulfman et al. | |
| 2019/0350703 A1 | 11/2019 | Weber et al. | |

FOREIGN PATENT DOCUMENTS

| | | |
|---|---|---|
| CN | 101690683 | 4/2010 |
| CN | 103628147 | 3/2014 |
| CN | 104780952 | 7/2015 |
| EP | 3316818 | 5/2019 |
| JP | H0654868 | 3/1994 |
| JP | 2013144009 | 7/2013 |
| WO | 0224119 | 3/2002 |
| WO | 02074201 | 9/2002 |
| WO | 2004080346 | 2/2005 |
| WO | 2005039664 | 5/2005 |
| WO | 2006000763 | 1/2006 |
| WO | 2008097592 | 8/2008 |
| WO | 2009038761 | 3/2009 |
| WO | 2010020660 | 2/2010 |
| WO | 2010048281 | 4/2010 |
| WO | 2014008207 | 1/2014 |
| WO | 2014143866 | 9/2014 |
| WO | 2014149319 | 9/2014 |
| WO | 2014158444 | 10/2014 |
| WO | 2016025945 | 2/2016 |
| WO | 2016164197 | 10/2016 |
| WO | 2016164209 | 10/2016 |
| WO | 2017004035 | 1/2017 |
| WO | 2017011392 | 1/2017 |
| WO | 2017048575 | 3/2017 |
| WO | 2017200920 | 11/2017 |
| WO | 2018200378 | 11/2018 |

OTHER PUBLICATIONS

"Non-Final Office Action," for U.S. Appl. No. 14/656,044 dated Mar. 17, 2017 (34 pages).

"Response to Communication Pursuant to Article 94(3) EPC," for European Patent Application No. 13739321.1 filed with the EPO Jan. 2, 2017 (37 pages).

Aksoy, Ayse E. et al., "Surface Modification of Polyurethanes with Covalent Immobilization of Heparin," Macromolecular Symposia, vol. 269, Issue 1, pp. 145-153, Aug. 2008 (9 pages).

Alferiev, Ivan et al., "Prevention of polyurethane valve cusp calcification with covalently attached bisphosphonate diethylamino moieties," J Biomed Mater Res 66A: 385-395, 2003 (11 pages).

Athappan, Ganesh et al., "Influence of Transcatheter Aortic Valve Replacement Strategy and Valve Design on Stroke After Transcatheter Aortic Valve Replacement: A Meta-Analysis and Systematic Review of Literature," J Am Coll Cardiol. 2014;63(20):2101-2110 (10 pages).

Barkoula, Nektaria-Marianthi et al., "Processing of Single Polymer Composites Using the Concept of Constrained Fibers," Polymer Composites, 2005, 26: p. 114-120 (7 pages).

Bastiaansen, Cees W. et al., "Melting Behavior of Gelspun-Drawn Polyolefins," Makromol. Chem., Macromol. Symp., 1989. 28: p. 73-84 (12 pages).

Bates, Frank S. et al., "Multiblock Polymers: Panacea or Pandora's Box?," SCIENCE, 2012, 336:434-440 (7 pages).

(56) References Cited

OTHER PUBLICATIONS

Bernacca, Gillian M. et al., "Mechanical and morphological study of biostable polyurethane heart valve leaflets explanted from sheep," J Biomed Mater Res 61:138-145, 2002 (8 pages).
Bhattacharyya, D. et al., "Polyamide 6 single polymer composites," eXPRESS Polym. Lett., 2009. 3(8): p. 525-532 (8 pages).
Cacciola, G. et al., "A synthetic fiber-reinforced stentless heart valve," Journal of Biomechanics, Jan. 1, 2000 (Jan. 1, 2000), pp. 653-658, XP055284947, Retrieved from the Internet: URL:http://ac.els-cdn.com/ (6 pages).
Cacciola, G. et al., "A three-dimesional mechanical analysis of a stentless fibre-reinforced aortic valve prosthesis," Journal of Biomechanics, Jan. 1, 2000 (Jan. 1, 2000), pp. 521-530, XP055284955, Retrieved from the Internet: URL:http://ac.els-cdn.com/ (10 pages).
Charles, Lyndon F. et al., "Self-reinforced composites of hydroxyapatite-coated PLLA fibers: fabrication and mechanical characterization," J. Mech. Behav. Biomed. Mater., 2013. 17: p. 269-277 (9 pages).
Claiborne, Thomas E. et al., "In Vitro Evaluation of a Novel Hemodynamically Optimized Trileaflet Polymeric Prosthetic Heart Valve," Journal of Biomechanical Engineering 2013, vol. 135 (8 pages).
"Communication Pursuant to Rules 161(1) and 162 EPC," for EP Patent Application No. 13739321.1-1455 dated Feb. 18, 2015 (2 pages).
De Yoreo, James J. et al., "Principles of Crystal Nucleation and Growth," Biomineralization, Mineral Soc. Am., Washington, DC, 2003, pp. 57-93 (37 pages).
Dencheva, Nadya et al., "Structure-properties relationship in single polymer composites based on polyamide 6 prepared by in-mold anionic polymerization," J. Mater. Sci., 2013. 48(20): p. 7260-7273 (14 pages).
Duhovic, Miro P. et al., "Polyamide 66 polymorphic single polymer composites," Open Macromol. J., 2009. 3: p. 37-40. (4 pages).
Fakirov, Stoyko "Nano- and Microfibrillar Single-Polymer Composites: A Review," Macromol. Mater. Eng., 2013. 298(1): p. 9-32 (24 pages).
Feng, Yakai et al., "Surface modification of polycarbonate urethane by covalent linkage of heparin with a PEG spacer," Transactions of Tianjin University, Feb. 2013, vol. 19, Issue 1, pp. 58-65 (8 pages).
"First Office Action," for Chinese Patent Application No. 201380044842.0 dated Dec. 18, 2015 (15 pages) with English Translation.
Gallocher, "Durability Assessment of Polymer Trileaflet Heart Valves," (2007). FIU Electronic Theses and Dissertations. Paper 54 (237 pages).
Généreux, Philippe et al., "Vascular Complications After Transcatheter Aortic Valve Replacement: Insights from the PARTNER Trial," J Am Coll Cardiol. 2012;60(12):1043-1052 (10 pages).
"Glycosaminoglycan," Wikipedia, posted on or before Oct. 16, 2004, retrieved Feb. 13, 2014, http://en.wikipedia.org/wiki/Glycosaminoglycan, 6 pages.
Gong, Ying et al., "Polyamide single polymer composites prepared via in situ anionic polymerization of ε-caprolactam," Composites, Part A, 2010. 41A(8): p. 1006-1011 (6 pages).
Gong, Ying et al., "Single polymer composites by partially melting recycled polyamide 6 fibers: preparation and characterization," J. Appl. Polym. Sci., 2010. 118(6): p. 3357-3363 (7 pages).
Goyal, R. K. et al., "High performance polymer composites on PEEK reinforced with aluminum oxide," J. Appl. Polym. Sci., 2006. 100(6): p. 4623-4631 (9 pages).
Han, Dong K. et al., "In vivo biostability and calcification-resistance of surface-modified PU-PEO—SO3," Journal of Biomedical Materials Research, vol. 27, 1063-1073, 1993 (11 pages).
Hine, P.J. et al., "High stiffness and high impact strength polymer composites by hot compaction of oriented fibers and tapes.," in Mechanical Properties of Polymers Based on Nanostructure and Morphology, CRC Press, 2005 (45 pages).
Hine, P.J. et al., "Hot compaction of woven nylon 6,6 multifilaments," J. Appl. Polym. Sci., 2006. 101(2): p. 991-997 (7 pages).
Hine, P.J. et al., "Hot Compaction of Woven Poly(ethylene terephthalate) Multifilaments," J. Appl. Polym. Sci., 2004. 91(4): p. 2223-2233 (11 pages).
Hine, P.J. et al., "Hybrid carbon fibre/nylon 12 single polymer composites," Composites Part A: Applied Science and Manufacturing 65 (2014) (17 pages).
"International Preliminary Report on Patentability," for International Application No. PCT/US2013/048976 dated Jan. 6, 2015 (9 pages).
"International Search Report & Written Opinion," for International Application No. PCT/US2013/048976 dated Nov. 19, 2013 (20 pages).
"International Search Report and Written Opinion," for PCT/US2016/024614 dated Jul. 12, 2016 (13 pages).
"International Search Report and Written Opinion," for PCT/US2016/024753 dated Jul. 22, 2016 (11 pages).
Jiang, Shaoyi et al., "Ultralow-Fouling, Functionalizable, and Hydrolyzable Zwitterionic Materials and Their Derivatives for Biological Applications," Adv Mater. Mar. 5, 2010;22(9):920-32 (13 pages).
Kaflon-Cohen, Estelle et al., "Microstructure and nematic transition in thermotropic liquid crystalline fibers and their single polymer composites," Polym. Adv. Technol., 2007. 18(9): p. 771-779 (9 pages).
Kalejs, et al., "St. Jude Epic heart valve bioprostheses versus native humand and porcine aortic valves—comparison of mechanical properties," Interactive Cardiovascular and Thoracic Surgery 8 (2009) 553-557 (5 pages).
Kang, Jungmee et al., "Polyisobutylene-Based Polyurethanes with Unprecedented Properties and How They Came About," Journal of Polymer Science Part A: Polymer Chemistry, 2011. 49(18): p. 3891-3904 (14 pages).
Khondker, O.A. et al., "Fabrication and mechanical properties of aramid/nylon plain knitted composites," Composites Part A: Applied Science and Manufacturing, 2004. 35(10): p. 1195-1205 (11 pages).
Kim, Nam K. et al., "Nanofibrillar Poly(vinylidene fluoride): Preparation and Functional Properties," Int. J. Polym. Mater. Polym. Biomater., 2014. 63(1): p. 23-32 (10 pages).
Kim, Nam K. et al., "Polymer-Polymer and Single Polymer Composites Involving Nanofibrillar Poly(vinylidene Fluoride): Manufacturing and Mechanical Properties," J. Macromol. Sci., Part B: Phys., 2014. 53(7): p. 1168-1181 (14 pages).
"Liquid-Crystal Polymer," Wikipedia, the Free Encyclopedia <http://en/wikipedia.org/wiki/Liquid-crystal_polymer>, retrieved Jun. 2, 2016 (3 pages).
Liu, et al., "Effect of fiber orientation on the stress distribution within a leaflet of a polymer composite heart valve in the closed position," J of Biomedichanics, 2007, 40:1099-1106 (8 pages).
Maity, J. et al., "Homocomposites of chopped fluorinated polyethylene fiber with low-density polyethylene matrix," Mater. Sci. Eng., A, 2008. A479(1-2): p. 125-135 (11 pages).
Masoumi, et al., "Trilayered Elastomeric Scaffolds for Engineering Heart Valve Leaflets," Biomaterials. Sep. 2014; 35(27):7774-7785 (28 pages).
Matabola, K. P. et al., "Single polymer composites: a review," Journal of Materials Science, 2009. 44(23): p. 6213-6222 (10 pages).
Medeiros Araujo, Thiago et al., "Liquid crystalline single-polymer short-fibers composites," Composite Interfaces, 2013. 20(4): p. 287-298 (12 pages).
"Non-Final Office Action," for U.S. Appl. No. 14/656,044, dated May 20, 2016 (20 pages).
Ohri, Rachit et al., "Hyaluronic acid grafting mitigates calcification of glutaraldehyde-fixed bovine pericardium," J Biomed Mater Res 70A: 328-334, 2004 (7 pages).
"Response to Non-Final Office Action," for U.S. Appl. No. 14/656,044, dated May 20, 2016 and filed Aug. 9, 2016 (11 pages).
Schneider, Tobias et al., "Influence of fiber orientation in electrospun polymer scaffolds on viability, adhesion and differentiation of articular chondrocytes," Clinical Hemorheology and Microcirculation 52 (2012) 325-336 (13 pages).
Sun, Xiaoli et al., "α and β Interfacial Structures of the iPP/PET Matrix/Fiber Systems," Macromolecules, 2007. 40(23): p. 8244-8249 (6 pages).

(56) References Cited

OTHER PUBLICATIONS

Vesely, et al., "Micromechanics of the fibrosa and the ventricularis in aortic valve leaflets," J Biomech. 1992 25(1)101-113 (12 pages).
Vick, Linda W. et al., "Hot compaction and consolidation of polycarbonate powder," Polym. Eng. Sci., 1998. 38(11): p. 1824-1837 (14 pages).
Wang, Qiang et al., "A novel small animal model for biocompatibility assessment of polymeric materials for use in prosthetic heart valves," J Biomed Mater Res 93A: 442-453, 2010 (12 pages).
Wang, Qiang et al., "In-Vivo Assessment of a Novel Polymer (SIBS) Trileaflet Heart Valve," J Heart Valve Dis, Jul. 2010, 19(4):499-505 (7 pages).
Ward, I.M. et al., "Developments in oriented polymers," Plastics, Rubber and Composites, 2004. 33(5): p. 189-194 (6 pages).
Ward, I.M. et al., "Novel composites by hot compaction of fibers," Polym. Eng. Sci., 1997. 37(11): p. 1809-1814 (6 pages).
Wheatley, et al., "Polyurethane: material for the next generation of heart valve prostheses?," Eur J Cardio-Thoracic Surg, 2000, 17:440-448 (11 pages).
Yang, Mingjing et al., "Assessing the Resistance to Calcification of Polyurethane Membranes Used in the Manufacture of Ventricles for a Totally Implantable Artificial Heart," J Biomed Mater Res (Appl Biomater) 48: 648-659, 1999 (12 pages).
Yao, Jian et al., "High Strength and High Modulus Electrospun Nanofibers," Fibers 2014; 2:158-187 (30 pages).
Yeh, Shiou-Bang et al., "Modification of Silicone Elastomer with Zwitterionic Silane for Durable Antifouling Properties," Langmuir 2014, 30, 11386-11393 (8 pages).
Zhang, Baoyan et al., "Studies of Novel Segmented Copolyether Polyurethanes," Eur. Polym. J., vol. 34, No. 3-4, pp. 571-575 (1998) (5 pages).
Zhang, Zhiping et al., "Effect of Crosslinking and Grafting by 60Co-γ-ray Irradiation on Carbon Black/Polyethylene Switching Materials and Fluoride Resin System in self-regulating Heating Cables," JAERI-Conf, 2000. 2000-001(JCBSRC '99, the 8th Japan-China Bilateral Symposium on Radiation Chemistry, 1999): p. 202-210 (9 pages).
Zhao, Zeng Hua et al., "Research development of single polymer composite preparation," Gongcheng Suliao Yingyong, 2010. 38(2): p. 81-84, with machine translation (11 pages).
"Communication Pursuant to Article 94(3) EPC," for European Patent Application No. 13739321.1 dated Sep. 8, 2016 (4 pages).
"Final Office Action," for U.S. Appl. No. 14/656,044 dated Sep. 9, 2016 (17 pages).
"International Search Report and Written Opinion," for PCT Application No. PCT/US2016/041757 dated Oct. 12, 2016 (12 pages).
"International Search Report and Written Opinion," for PCT/US2016/039808 dated Sep. 26, 2016 (11 pages).
Kuang, Jinghao et al., "Universal Surface-initiated Polymerization of Antifouling Zwitterionic Brushes Using a Mussel Mimetic Peptide Initiator," Langmuir. May 8, 2012; 28(18): 7258-7266 (20 pages).
"Response to Final Office Action," for U.S. Appl. No. 14/656,044, dated Sep. 9, 2016 and filed Dec. 8, 2016 (9 pages).
"Second Office Action," for Chinese Patent Application No. 201380044842.0, dated Aug. 12, 2016 (16 pages) with summary.
Tu, Qin et al., "Synthesis of polyethylene glycol- and sulfobetaine-conjugated zwitterionic poly(l-lactide) and assay of its antifouling properties," Colloids and Surfaces B; Biointerfaces 102 (2013) 331-340 (10 pages).
"Decision of Final Rejection," for China Patent Application No. 201380044842.0, dated Apr. 7, 2017 (18 pages) with Summary.
"International Preliminary Report on Patentability," for PCT Application No. PCT/US2016/024614 dated Oct. 19, 2017 (7 pages).
"International Preliminary Report on Patentability," for PCT Application No. PCT/US2016/024753 dated Oct. 19, 2017 (7 pages).
"International Preliminary Report on Patentability," for PCT Application No. PCT/US2016/039808 dated Jan. 11, 2018 (8 pages).
"International Preliminary Report on Patentability," for PCT Application No. PCT/US2016/041757 dated Jan. 25, 2018 (8 pages).

"Response to Non-Final Office Action," for U.S. Appl. No. 14/656,044 dated Mar. 17, 2017 and filed Jun. 8, 2017 (11 pages).
Berkland, Cory et al., "Controlling surface nano-structure using flow-limited field-injection electrostatic spraying (FFESS) of poly(D,L-lactide-co-glycolide)," Biomaterials (2004) 25: 5649-5658 (10 pages).
Fabreguette, et al., "X-ray mirrors on flexible polymer substrates fabricated by atomic layer deposition," Thin Solid Films 515: 7177-7180 (2007), 5 pages.
Fabreguette, Francois H. et al., "Ultrahigh x-ray reflectivity from W/Al2O3 multilayers fabricated using atomic layer deposition," Applied Physics Letters 88: 013166 (2006), 3 pages.
"File History," for U.S. Appl. No. 13/932,968.
George, "Final Report—Fabrication of Nanolaminates with Ultrathin Nanolayers Using Atomic Layer Deposition: Nucleation & Growth Issues," AFOSR Grant No. FA9550-01-1-0075 Feb. 2009 (36 pages).
Groner, M. D. et al., "Gas Diffusion Barriers on Polymers Using Al2O3 Atomic Layer Deposition," Applied Physics Letters 88, 051907, 2006 (3 pages).
Hass, D. D. et al., "Reactive vapor deposition of metal oxide coatings," Surface and Coatings Technology 146-147 (2001) 85-93, 9 pages.
"International Search Report and Written Opinion," for PCT Application No. PCT/US2017/032656 dated Jul. 21, 2017 (16 pages).
Jen, Shih-Hui et al., "Critical tensile and compressive strains for cracking of Al2O3 films grown by atomic layer deposition," Journal of Applied Physics 109, 084305 (2011), 11 pages.
Jen, Shih-Hui et al., "Critical tensile strain and water vapor transmission rate for nanolaminate films grown using Al2O3 atomic layer deposition and alucone molecular layer deposition," Applied Physics Letters 101, 234103 (2012), 3 pages.
Mach, H. et al., "Highly Reactive Polyisobutene as a Component of a New Generation of Lubricant and Fuel Additives," Lubrication Science 1999, 11 (2), 175-185 (11 pages).
"Non-Final Office Action," for U.S. Appl. No. 15/082,239 dated May 16, 2018 (34 pages).
"Non-Final Office Action," for U.S. Appl. No. 15/082,293 dated Jul. 11, 2018 (41 pages).
"Notification of Patent Reexamination," for Chinese Patent Application No. 201380044842.0 dated Feb. 7, 2018 (12 pages) with English summary.
Raghavan, R. et al., "Nanocrystalline-to-amorphous transition in nanolaminates grown by low temperature atomic layer deposition and related mechanical properties," Applied Physics Letters 100, 191912 (2012), 9 pages.
"Response to Communication Pursuant to Rules 161(1) and 162 EPC," for European Patent Application No. 16715218.0 filed May 25, 2018, 13 pages.
"Response to Communication Pursuant to Rules 161(1) and 162 EPC," for European Patent Application No. 16715724.7 filed May 25, 2018, (7 pages).
"Response to Communication Pursuant to Rules 161(1) and 162 EPC," for European Patent Application No. 16736720.0 filed with the EPO Jul. 12, 2018 (12 pages).
"Response to Non-Final Office Action," for U.S. Appl. No. 15/257,211, dated Apr. 10, 2018 and filed Jun. 18, 2018 (10 pages).
"Response to Non-Final Office Action," for U.S. Appl. No. 15/082,239, dated May 16, 2018 and filed Jun. 19, 2018 (13 pages).
Rutledge, G.C. et al., "Electrostatic Spinning and Properties of Ultrafine Fibers," National Textile Center Annual Report: Nov. 2001, M01-D22, (10 pages).
Shin, Y. M. et al., "Experimental characterization of electrospinning: the electrically forced jet and instabilities," Polymer 42 (2001) 9955-9967 (13 pages).
Szeghalmi, Adriana et al., "All dielectric hard x-ray mirror by atomic layer deposition," Applied Physics Letters 94, 133111 (2009), 3 pages.
Szilagyi, Imre M. et al., "Review on One-Dimensional Nanostructures Prepared by Electrospinning and Atomic Layer Deposition," INERA Workshop of ISCMP2014, IOP Publishing, Journal of Physics: Conference Series 559, 2014 (13 pages).
"International Preliminary Report on Patentability," for PCT Application No. PCT/US2016/050691 dated Mar. 29, 2018 (9 pages).

(56) References Cited

OTHER PUBLICATIONS

"Non-Final Office Action," for U.S. Appl. No. 15/257,211 dated Apr. 10, 2018 (39 pages).
Final Office Action for U.S. Appl. No. 15/082,239 dated Oct. 12, 2018 (19 pages).
Final Office Action for U.S. Appl. No. 15/257,211 dated Jul. 26, 2018 (13 pages).
International Search Report and Written Opinion for PCT Application No. PCT/US2018/028864 dated Jul. 30, 2018 (10 pages).
Madhusha, "Difference between Fluorine and Fluoride," Aug. 9, 2017, pediaa.com, pp. 1-8. URL <http://pediaa.com/difference-between-fluorine-and-fluoride/> (8 pages).
Non-Final Office Action for U.S. Appl. No. 15/082,382 dated Sep. 19, 2018 (42 pages).
Non-Final Office Action for U.S. Appl. No. 15/595,176 dated Aug. 27, 2018 (30 pages).
Non-Final Office Action for U.S. Appl. No. 15/797,394 dated Sep. 26, 2018 (39 pages).
Notice of Allowance for U.S. Appl. No. 15/257,211 dated Sep. 24, 2018 (7 pages).
Response to Final Rejection dated Jul. 26, 2018, for U.S. Appl. No. 15/257,211, submitted via EFS-Web on Aug. 9, 2018.
Response to Non-Final Rejection dated Jul. 11, 2018, for U.S. Appl. No. 15/028,293, submitted via EFS-Web on Oct. 11, 2018, 12 pages.
Final Office Action for U.S. Appl. No. 15/797,394 dated Jan. 30, 2019 (12 pages).
First Office Action for Chinese Patent Application No. 201680040898.2 dated Feb. 28, 2019 (14 pages). No English Translation.
First Office Action for Chinese Patent Application No. 201680053293.7 dated Mar. 5, 2019 (7 pages) with English summary by the Associate.
Non-Final Office Action for U.S. Appl. No. 15/082,239 dated Apr. 4, 2019 (12 pages).
Notice of Allowance for U.S. Appl. No. 15/082,239 dated May 22, 2019 (11 pages).
Notice of Allowance for U.S. Appl. No. 15/082,293 dated Jan. 17, 2019 (12 pages).
Notice of Allowance for U.S. Appl. No. 15/082,382 dated Jan. 25, 2019 (14 pages).
Notice of Allowance for U.S. Appl. No. 15/205,098 dated May 2, 2019 (16 pages).
Notice of Allowance for U.S. Appl. No. 15/959,176 dated Mar. 21, 2019 (13 pages).
Response to Communication Pursuant to Rules 161(1) and 162 EPC for European Patent Application No. 17725140.2 filed Apr. 2, 2019 (9 pages).
Response to Final Rejection dated Jan. 30, 2019, for U.S. Appl. No. 15/797,394, submitted via EFS-Web on Apr. 23, 2019, 8 pages.
Response to Final Rejection dated Oct. 12, 2018, and Advisory Action dated Jan. 22, 2019, for U.S. Appl. No. 15/082,239, submitted via EFS-Web on Feb. 12, 2019, 7 pages.
Response to Non-Final Rejection dated Apr. 4, 2019 for U.S. Appl. No. 15/082,239, submitted via EFS-Web on May 10, 2019, 6 pages.
Third Office Action for Chinese Patent Application No. 201380044842.0 dated Dec. 29, 2018 (12 pages), with English translation.
Lane, Bobby. "What Line Should I Use?," Bassmaster.com (www.bassmaster.com/tips/ask-experts-what-line-should-i-use) Apr. 2013, pp. 1-7.
Mckenna, H. A. et al., "Handbook of Fibre Rope Technology," The Textile Institute, Woodhead Publishing Limited, Cambridge England 2004, pp. 1-432.
Mitchell, J. "Braided Fishing Lines (Superlines)," Sufix Fishing Lines Product page as it appeared Apr 5, 2019 (https://sufix.fishing/braided-fishing-lines-superlines), pp. 1-5.
"Why Use Superlines?," Berkley-Fishing.com (www.berkley-fishing.com/Berkley-ae-why-use-superlines.html), pp. 1-6.
First Office Action for Chinese Patent Application No. 20160036250.8 dated Nov. 2, 2018 (11 pages) with English Summary.
First Office Action for Chinese Patent Application No. 201680018700.0 dated Nov. 2, 2018 (12 pages) with English Summary.
International Preliminary Report on Patentability for PCT Application No. PCT/US2017/032656 dated Nov. 29, 2018 (7 pages).
Non-Final Office Action for U.S. Appl. No. 15/205,098 dated Oct. 30, 2018 (42 pages).
Response to Communication Pursuant to Rules 161(1) and 162 EPC for European Patent Application No. 16766455.6 filed Dec. 4, 2018 (9 pages).
Response to Final Rejection dated Oct. 12, 2018, for U.S. Appl. No. 15/082,239, submitted via EFS-Web on Dec. 17, 2018, 9 pages.
Response to Non Final Office Action for U.S. Appl. No. 15/205,098, filed Dec. 27, 2018 (7 pages).
Response to Non-Final Rejection dated Aug. 27, 2018, for U.S. Appl. No. 15/595,176, submitted via EFS-Web on Nov. 26, 2018, 6 pages.
Response to Non-Final Rejection dated Sep. 19, 2018, for U.S. Appl. No. 15/082,382, submitted via EFS-Web on Dec. 18, 2018, 6 pages.
Response to Non-Final Rejection dated Sep. 26, 2018, U.S. Appl. No. 15/797,394, submitted via EFS-Web on Dec. 19, 2018, 9 pages.
Second Office Action for Chinese Patent Application No. 201680018700.0 dated Jul. 12, 2019 (8 pages) No English Translation.
Second Office Action for Chinese Patent Application No. 201680036250.8 dated Jul. 11, 2019 (4 pages) No English Translation.
Communication Pursuant to Article 94(3) EPC for European Patent Application No. 16715218.0 dated Feb. 14, 2020 (6 pages).

\* cited by examiner

PROSTHETIC HEART VALVE COMPOSED OF COMPOSITE FIBERS

This application claims the benefit of U.S. Provisional Application No. 62/188,201 filed Jul. 2, 2015, the contents of which are herein incorporated by reference.

TECHNICAL FIELD

The present invention relates to prosthetic heart valve devices composed of composite fibers and methods relating thereto.

BACKGROUND

More than 250,000 heart valves are replaced worldwide each year due to structural defects such as valve stenosis that may lead to regurgitation. Valve stenosis is a condition where a heart valve is not able to fully open when blood is pumped through the heart because the heart valve leaflets are too stiff or fused together. Valve stenosis creates a narrowed opening that stresses the heart that can cause fatigue and dizziness in a patient. Regurgitation, which is a backward flow of blood, can reduce efficiency in blood pumping and cause the patient fatigue and shortness of breath.

There are currently two major types of valves that can be used for diseased heart valve replacement: a mechanical valve and a bioprosthetic valve. Mechanical valves demonstrate long term durability, but are associated with lifelong anti-coagulant treatments that prevent thrombus formation caused by the contact between a patient's blood and the valve materials. Bioprosthetic heart valves are typically constructed from porcine heart valves or from bovine or porcine pericardium. Bioprosthetic heart valves do not need anticoagulation, but are vulnerable to structural deterioration caused by calcification that results in the narrowing of the valve orifice and/or cusp tearing. As a result, surgeons may use mechanical heart valves for younger patients to avoid the device replacement risks associated with bioprosthetic heart valves. There continues to be a need for a heart valve that can be used for long term implantation.

SUMMARY

Disclosed herein are various embodiments of prosthetic heart valve devices and systems made of synthetic composite materials and methods related thereto. More specifically, prosthetic heart valve devices and systems composed of composite fibers and methods of making composite fibers are provided herein.

In Example 1, a prosthetic heart valve leaflet has a fiber-reinforced structure including a plurality of composite fibers. Each composite fiber includes a core fiber and a sheathing fiber disposed about the core fiber in which the core fiber or the sheathing fiber has a curvilinear shape.

In Example 2, the prosthetic heart valve leaflet of Example 1, wherein the sheathing fiber has the curvilinear shape, the sheathing fiber being spirally disposed about the core fiber.

In Example 3, the prosthetic heart valve leaflet of Example 1 or Example 2, wherein the sheathing fiber helically wraps around a longitudinal axis defined by the composite fiber.

In Example 4, the prosthetic heart valve leaflet of Examples 1-3, wherein a ratio of core diameter to sheathing fiber diameter ranges from about 1:1 to 1:2.

In Example 5, the prosthetic heart valve leaflet of Examples 1-4, wherein weight ratio of the core fibers to the sheathing fibers ranges from 0.2 to 5.0.

In Example 6, the prosthetic heart valve leaflet of Examples 1-5, wherein the core fiber and the sheathing fiber are made of different polymeric materials.

In Example 7, the prosthetic heart valve leaflet of Examples 1-6, wherein the core fiber includes an elastomer and the sheathing fiber includes a thermoplastic polymer.

In Example 8, the prosthetic heart valve leaflet of Examples 1-7, wherein the core fiber includes a tensile modulus that is greater than a tensile modulus of the sheathing fiber.

In Example 9, the prosthetic heart valve leaflet of Examples 1-8, wherein the core fiber or the sheathing fiber includes carbon fillers.

In Example 10, the prosthetic heart valve leaflet of Examples 1-9, wherein the composite fiber includes a coating including polyethylene glycol.

In Example 11, the prosthetic heart valve leaflet of Examples 1-10, wherein the composite fiber includes at least two sheathing fibers spirally disposed about the core fiber.

In Example 12, the prosthetic heart valve leaflet of Examples 1-11, wherein the at least two sheathing fibers are spirally disposed about one another and the core fiber.

In Example 13, the prosthetic heart valve leaflet of Example 1, wherein the core fiber is encapsulated within the sheathing fiber, the core fiber having an undulating shape within the sheathing fiber relative to a longitudinal axis defined by the composite fiber.

In Example 14, the prosthetic heart valve leaflet of Example 13, wherein the core has the undulating shape within the sheathing fiber when the fiber is in a relaxed state, but a straight shape within the sheathing fiber when the composite fiber is stretched in a strained state.

In Example 15, the prosthetic heart valve leaflet of Example 13 or Example 14, wherein the composite fibers are electrospun composite fibers.

In Example 16, the prosthetic heart valve leaflet of Examples 13-15, wherein a ratio of a core fiber diameter to a sheathing fiber thickness ranges from 0.2 to 5.0.

In Example 17, the prosthetic heart valve leaflet of Examples 13-16, wherein the core fiber includes a thermoplastic polymer and the sheathing fiber includes an elastomeric core.

In Example 18, a method of forming a prosthetic heart valve material includes forming composite fibers. Each composite fiber is formed by spirally wrapping a sheathing fiber about a core fiber.

In Example 19, the method of Example 18, wherein forming a portion of the composite fiber includes using an emulsion electrospinning process, a coaxial electro spinning process, or co-electrospinning multiple polymers simultaneously.

In Example 20, the method of Example 18 or Example 19, further including forming a fiber-reinforced structure by disposing a plurality of composite fibers within a polymer matrix.

Particular embodiments of the subject matter described in this document can be implemented to optionally provide one or more of the following advantages.

BRIEF DESCRIPTION OF THE DRAWINGS

FIGS. 3A and 3B are views of an exemplary composite fiber provided herein.

FIGS. 4A and 4B are views of another exemplary composite fiber provided herein.

FIGS. 6A and 6B provide illustrations of another exemplary composite fiber provided herein and components thereof.

DETAILED DESCRIPTION

Figure 1:
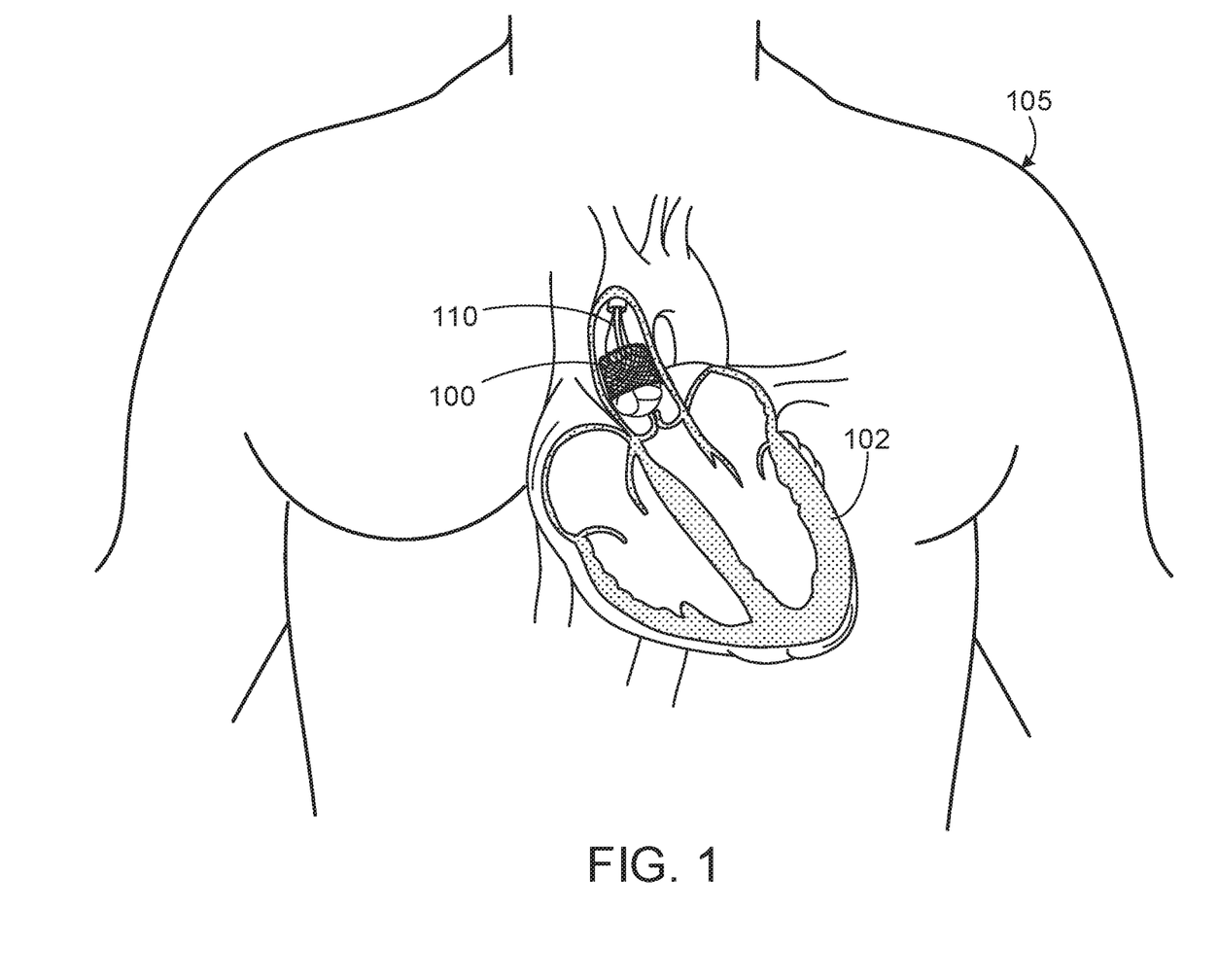
FIG. 1 is an illustration of an exemplary prosthetic heart valve provided herein within a human anatomy.

FIG. 1 is an illustration of a prosthetic heart valve 100 provided herein within a heart 102 of a human body 105. The heart 102 has four heart valves: a pulmonary valve, a tricuspid valve, an aortic valve and a mitral valve. The heart valves allow blood to pass through the heart 102 and into major blood vessels connected to the heart 102, for example, the aorta and pulmonary artery. Prosthetic heart valve 100 of FIG. 1 is an aortic prosthetic heart valve that can be surgically implanted or delivered through blood vessels using a delivery device or catheter 110. The delivery catheter 110 can be inserted into a femoral, subclavian, or an aortic incision during a transcatheter aortic valve replacement (TAVR) procedure. Once inserted, the delivery catheter 110 can deliver the prosthetic heart valve 100 to a desired location within the anatomy and release the implantable heart valve 100 at a target implantation site. Although FIG. 1 shows prosthetic heart valve 100 replacing an aortic valve, in some cases, prosthetic heart valve 100 can be a replacement for another type of heart valve (e.g., a mitral valve or a tricuspid valve).

Figure 2:
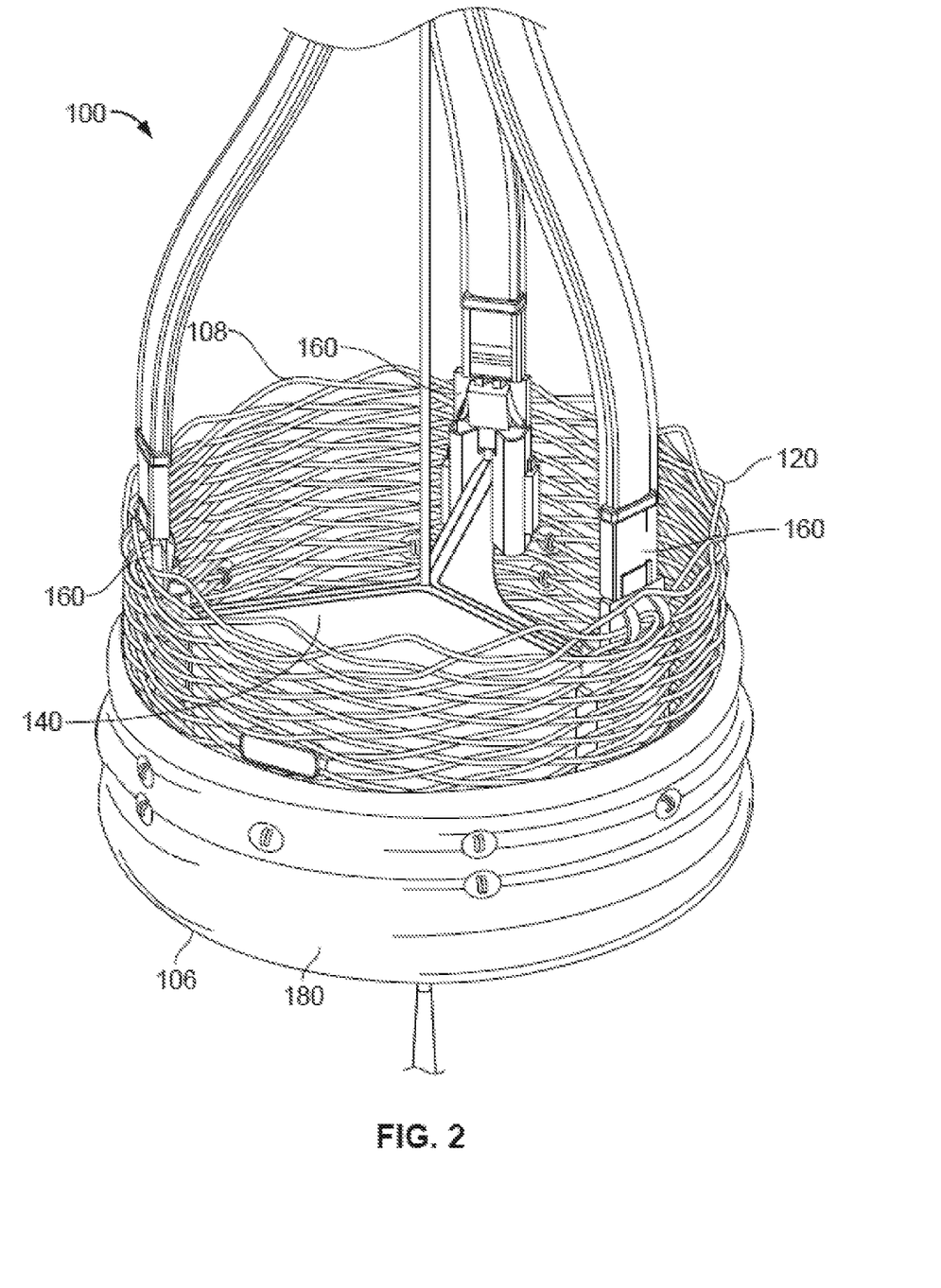
FIG. 2 is an enlarged view of the prosthetic heart valve of FIG. 1.

FIG. 2 provides a close up view of the prosthetic heart valve 100 and a distal end of the delivery catheter 110 of FIG. 1. The prosthetic heart valve 100 has a substantially tubular body 120, three leaflets 140, anchor elements 160 and a tubular seal 180. The tubular body 120 can be a radially expandable member, e.g. annular frame or stent, having an annular cavity. As shown in FIG. 2, the heart valve 100 can have a plurality of heart valve leaflets 140 coupled to the tubular body 120 within the annular cavity. Three anchor elements 160 positioned within the annular cavity of tubular body 120 can each secure the heart valve leaflets 140 to the tubular body 120. Each anchor element 160 can be coupled to the tubular body 120 with fasteners and coupled to the leaflets 140 with a clamping element. The tubular seal 180 can be disposed about a portion of the tubular body 120. In particular, the tubular seal 180 can have an outflow end portion 108 disposed about an outer surface of the tubular body 120 to restrict blood flow around the leaflets. The tubular seal 180 can also have an inflow end portion 106 secured to the bottom edges of the leaflets 140.

Prosthetic heart valve 100 can be made of various materials. In some cases, at least a portion of prosthetic heart valve 100, for example, the leaflets 140 or a portion of the tubular body 120, can be made of synthetic materials. In some cases, prosthetic heart valve 100 can be made entirely of synthetic materials. Suitable synthetic materials of prosthetic heart valve 100 can include, but are not limited to, polymeric materials, metals, ceramics, and combinations thereof. In some cases, synthetic materials of the prosthetic heart valve 100 can include a composite material composed of at least two constituent materials with different physical, mechanical and/or chemical properties. In some cases, synthetic materials of the prosthetic heart valve 100 provided herein can include a composite material composed of at least two constituent materials with different physical, mechanical and/or chemical properties In use, the prosthetic heart valve 100 provided herein can be implanted either surgically or through transcatheter delivery into the heart 102. The edge portions of the leaflets 140 can move into coaptation with one another in a closed position to substantially restrict fluid from flowing past the closed prosthetic heart valve 100. The edge portions of the leaflets 140 can alternatively move away from one another to an open position permitting fluid to flow past the prosthetic heart valve 100. Movement of the leaflets 140 between the closed and open positions can substantially approximate the hemodynamic performance of a healthy natural valve.

As the prosthetic heart valve 100 opens and closes during each heartbeat, each leaflet 140 flexes between an open and a closed position. Tensile and flexural strain on the leaflet 140 can change depending on its position. Leaflets 140 can therefore elongate in various directions as the valve 100 opens and closes. Each leaflet 140 can elongate in a radial direction and/or a circumferential direction with each heartbeat. Leaflets 140 can also elongate in directions that are directed at an oblique angle relative to the radial and circumferential directions. Due to the various directions of elongation that a prosthetic leaflet 140 can experience during use, the leaflet 140 can greatly benefit by being composed of materials with anisotropic physical and mechanical properties, in some cases.

In various embodiments, a prosthetic heart valve 100 can be made from a fiber-reinforced composite material. In some cases, the fiber-reinforced composite material can be composed of a plurality of fibers and a polymer matrix. In some cases, the plurality of fibers can be randomly oriented or orderly aligned within the polymer matrix. In some cases, fibers of the fiber-reinforced composite material can include a plurality of composite fibers. Each composite fiber is composed of two or more different materials. The composite fiber can have various structural configurations, as will be discussed further in subsequent sections.

Heart valve leaflets 140 composed of composite fibers can provide several advantages. For example, a prosthetic heart composed of composite fibers can provide desirable mechanical performance of two or more materials. In some cases, composite fibers can have structural arrangements that provide the leaflets 140 with anisotropic mechanical properties. Composite fiber may, in some cases, form more durable synthetic materials that can be used for manufacturing heart leaflets for younger patients requiring long term durability devices. A prosthetic heart valve 100 made of composite fibers may provide a thinner heart valve material that has the desired mechanical strength, while allowing for the reduction of the valve profile of the device during delivery and access through smaller orifices, such as smaller femoral sheaths or smaller blood vessels. In some cases, heart valve leaflets 140 can be composed of biocompatible composite fibers that can reduce or eliminate calcification and deterioration of the leaflets 140. In some cases, prosthetic heart valves 100 made of composite fibers may reduce the need for long term anticoagulation therapy. The use of composite fibers, in some cases, may reduce the risk of sourcing issues and infection that might be associated with animal tissues, such as bovine spongiform encephalopathy.

Figure 3A:
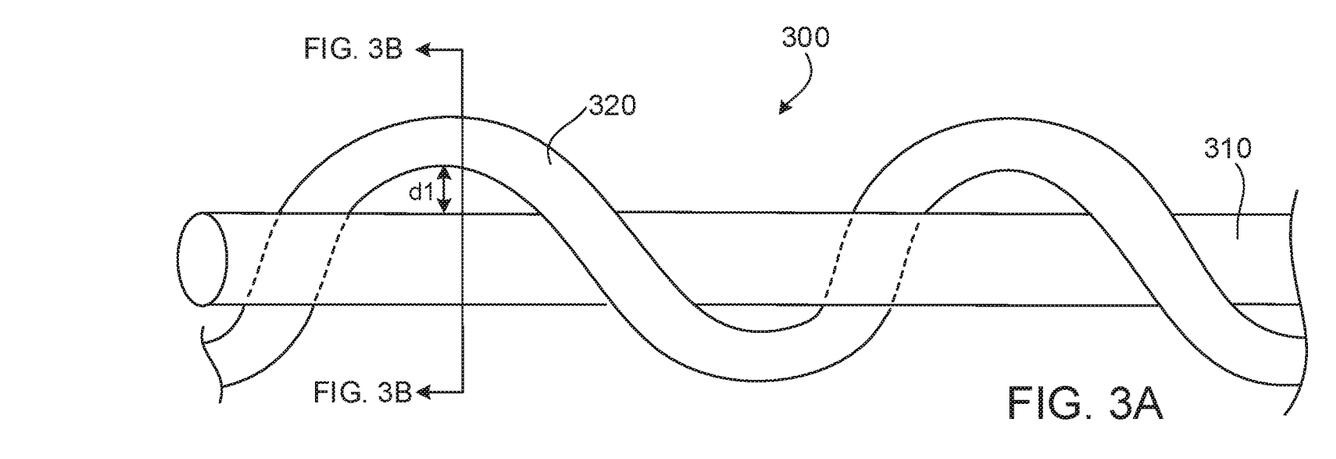
FIG. 3A provides a side perspective view of the composite fiber.
Figure 3B:
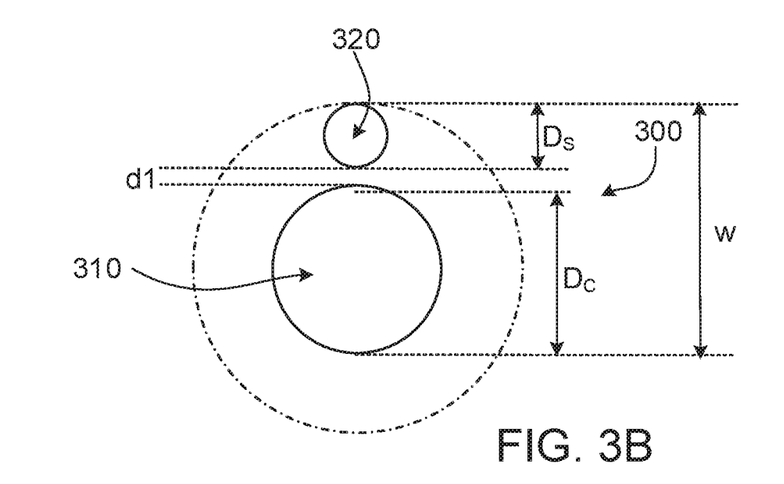
FIG. 3B provides a cross-sectional view of the composite fiber of FIG. 3A.

FIGS. 3A and 3B show an example of a composite fiber 300 provided herein of a prosthetic heart valve leaflet, such as the prosthetic heart valve leaflet 140 of FIG. 2. The depicted composite fiber 300 includes a core fiber 310 (which can also be described as an inner fiber) and a sheathing fiber 320 (which can also be described as an outer fiber or a cladding fiber) disposed about the core fiber 310. As shown, the sheathing fiber 320 may be a single fiber wrapped spirally around the core fiber 310. In some cases, the composite fiber 300 can include a core fiber 310 and a sheathing fiber 320 disposed about the core fiber 310 for at least a portion of a length of the composite fiber 300, or over an entire length of the composite fiber 300.

The sheathing fiber 320 can be bonded to the core fiber 310 in at least at two separate bonding locations. In some cases, the sheathing fiber 320 can be bonded at first and second bonding locations along the core fiber 310 in which the first and second locations are separated by a predetermined bonding distance along a longitudinal axis defined by the core fiber 310. In some cases, the predetermined bonding distance between the first and second locations can range between 1 millimeters (mm) and 100 mm, including all values and ranges therebetween. In some cases, the predetermined bonding distance can range from about 1 mm to about 5 mm, about 5 mm to about 10 mm, about 10 mm to about 20 mm, about 20 mm to about 30 mm, about 30 mm to about 40 mm, about 40 mm to about 50 mm, about 50 mm to about 100 mm. By bonding the sheathing fiber 320 in at least two separate locations, the core fiber 310 is allowed to initially elongate relatively independent of the sheathing fiber 320. The elasticity of the core fiber 310 therefore dominates the elastic characteristic of the composite fiber 300 during initial stretching until the loose sheathing fiber 320 becomes tautly wrapped about the core fiber 310. The predetermined bonding distance can be adjusted as desired to increase or decrease the maximum strain and elasticity of the composite fiber 300. In some cases, the sheathing fiber 320 can be bonded to the core fiber 310 in more than two bonding locations. For example, the sheathing fiber 320 can be bonded to the core fiber 310 in two, three, four, five, or greater than five locations along the core fiber 310.

Still referring to FIGS. 3A and 3B, the sheathing fiber 320 can be wrapped loosely around the core fiber 310, forming a gap between the sheathing fiber 320 and the core fiber 310. In some cases, the gap can be defined by a radial distance "d1" between an exterior surface of the core fiber 310 and an adjacent, exterior surface of the core fiber 310. In some cases, a radial distance d1 of the gap can range from about 1 nm to about 1 micron, also including all values or ranges therebetween. At least a portion of the composite fiber 300 may optionally include no gap between the sheathing fiber 320 and the core fiber 310 (e.g., the radial distance is equal to 0). In some cases, the radial distance d1 can be characterized in terms of a diameter of the core fiber "Dc," for example, the radial distance d1 of the gap can range between 0 and 5 times the diameter of the core fiber Dc, for example, the radial distance d1 of the gap can be 0, 0.25, 0.50, 0.75, 1, 2, 3, 4, 5, or more than 5 times the diameter of the core fiber Dc.

As shown in FIG. 3B, transverse dimensions such as a radial width "w" of the composite fiber 300 can vary depending on the position of the sheathing fiber 320 relative to the core fiber 310. The radial width w of the composite fiber 300 is dependent on the diameter of the core Dc and a diameter of the sheathing fiber "Ds." For instance, in some cases, the radial width w of the composite fiber 300 can range between the diameter of the core fiber Dc up to approximately an additive sum of the core and sheathing fiber diameters (Dc+Ds). In some cases, a gap exists between the core fiber 310 and the sheathing fiber 320 that can increase the radial width w of the composite fiber 300.

The ratio of the diameter of the core fiber Dc and the sheathing fiber diameter Ds, in some cases, can range from about 1:1 to about 10:1, in addition to all values and ranges therebetween. In some cases, the ratio of the core and sheathing fiber diameters (Dc:Ds) can range from about 1:10 to about 1:5, about 1:5 to about 1:4, about 1:4 to about 1:3, about 1:3 to about 1:2, about 1:2 to about 1:1, about 1:1 to about 2:1, from about 2:1 to about 3:1, from about 3:1 to about 4:1, from about 4:1 to about 5:1, about 5:1 to 10:1, from 1:10 to 10:1, from 1:5 to 5:1, from 1:4 to 4:1, from 1:3 to 3:1, from 1:2 to 2:1, from 1:10 to 5:1, from 1:10 to 4:1, 1:10 to 3:1, from 1:10 to 2:1, from 1:10 to 1:1, from 1:1 to 1:10, from 1:2 to 1:10, from 1:3 to 1:10, from 1:4 to 1:10, from 1:5 to 1:10, from 1:6 to 1:10, from 1:7 to 1:10, from 1:8 to 1:10, or from 1:9 to 1:10. The ratio of core and sheathing fibers diameters can allow the mechanical properties (e.g., elastic properties) of the composite fiber 300 to be adjusted as desired.

Composite fibers 300 can be composed of core fibers 310 and/or sheathing fibers 320 having diameters or average diameters of at least 1 micron (or 0.00004 inches). Core fibers 310 and/or sheathing fibers 320 can be, in some cases, in the range of about 1 micron to about 100 microns (or about 0.00004 inches to about 0.004 inches), including all ranges and values therebetween. In some cases, for example, suitable core fibers 310 and/or sheathing fibers 320 diameter sizes can include ranges of about 1 micron to 5 microns (or about 0.00004 inches to about 0.0002 inches), 5 microns to 10 microns (or 0.0002 inches to about 0.0004 inches), 10 microns to 20 microns (or 0.0004 inches to about 0.0008 inches), 20 microns to 50 microns (or 0.0008 inches to about 0.0020 inches), and 50 microns to 100 microns (or 0.002 inches to about 0.004 inches). In some cases, core fibers 310 and/or sheathing fibers 320 can have diameters in the range of about 1 microns to about 10 microns (or 0.0004 inches to about 0.0020 inches), including all ranges and values therebetween. In some cases, the core fibers 310 and/or sheathing fibers 320 made from polymers can range from about 5 microns to about 100 microns (or 0.00002 inches to about 0.0040 inches), from about 10 microns to about 75 microns (or 0.0004 inches to about 0.003 inches), from about 10 micron to about 50 microns (or 0.0004 inches to about 0.0020 inches), from about 20 microns to about 100 microns (or 0.0008 inches to about 0.0040 inches), from about 25 microns to about 200 microns (or 0.001 inches to about 0.008 inches), or from about 20 microns to about 50 microns (or 0.0008 inches to about 0.002 inches). In some cases, core fibers 310 and/or sheathing fibers 320, such as LCP fibers, can range from 0.5 microns (or 500 nanometers) to 5 microns (or about 0.00002 inches to about 0.00020 inches).

In some cases, composite fibers 300 can include core fibers 310 and/or sheathing fibers 320 having diameters or average diameters less than 1 micron, or 1000 nanometers (nm) (or 0.00004 inches). In some cases, core fibers and/or sheathing fibers diameters or average diameters can range from 1 nm to 1000 nm, including all ranges and values therebetween. For example, core fibers and/or sheathing fibers diameters can range from about 1 nm to 10 nm, 10 nm to 50 nm, 50 nm to 100 nm, 100 nm to 500 nm, and 500 nm to 1000 nm. In some cases, fiber diameters can range from 100 nm to 1000 nm, including all ranges and values therebetween. Core fibers and/or sheathing fibers diameter can significantly affect physical and/or mechanical properties of a composite material. In some cases, a core fiber and/or sheathing fiber diameter can be sized to obtain a composite fiber 300 having desired physical and/or mechanical properties of two or more materials. For example, increasing the core fibers and/or sheathing fibers diameter of an exemplary composite material can, in some cases, increase the tensile strength of the material.

Fiber-reinforced composite materials provided herein can be composed of composite fibers 300 that are aligned in an orderly pattern to form a woven fibrous structure. In some cases, composite fibers 300 of fiber-reinforced composite materials can be composed of individual composite fibers 300 randomly oriented within a polymer matrix to form a non-woven, fibrous structure. In some cases, fiber-reinforced composite materials are composed of electrospun, composite fibers 300. A non-woven, fibrous structure can provide an isotropic material that have the same mechanical properties in all directions while a woven, fibrous structure can produce an anisotropic material that has directionally dependent mechanical properties.

Fiber-reinforced composite materials provided herein can optionally include a polymer matrix embedded within and/or covering over a fibrous structure composed of composite fibers 300. In some cases, the polymer matrix can interpenetrate the fibrous structure such that at least a portion of the polymer matrix become disposed between voids or spaces formed between individual composite fibers 300 of the fibrous structure.

Fiber-reinforced composite materials can include composite fibers 300 embedded within a polymer matrix in at least one layer (or section) of the fiber-reinforced material, or throughout the entire fiber-reinforced material. In some cases, the fiber-reinforced composite material can be composed of a plurality of composite fibers 300 and the polymer matrix. In some cases, some portions of the fiber-reinforced composite material can contain composite fibers 300 and some portions of the fiber-reinforced composite material can include no composite fibers 300. In some cases, some portions of the fiber-reinforced composite material can contain the polymer matrix and some portions of the fiber-reinforced composite material can include no polymer matrix. In some cases, the fiber-reinforced composite material can include additional layers of polymer, which can include different polymers than the polymer in polymer matrix or the same polymer in the polymer matrix. In some cases, different layers of polymer can include different polymer fibers, such as non-composite fibers (e.g., a fiber made of a single polymer) or different composite fibers 300, and/or different fiber arrangements. In some cases, the fiber-reinforced composite material can have an arrangement of composite fibers 300 within the matrix that results in producing isotropic properties. In some cases, a heart leaflet can include a fiber-reinforced composite material composed of a plurality of fibers and polymer matrix throughout the entire leaflet to simplify manufacturing.

In some cases, a layer of composite fibers 300 can be formed within a fiber-reinforced composite material. In some cases, a single layer of composite fibers 300 can include more than one material. In some cases, the fiber-reinforced composite material can include multiple layers of composite fibers 300, for example, two, three, four, five or greater than five layers of composite fibers 300. In some cases, at least one layer of composite fibers 300 can be made of the same material, for example, a first polymer. In some cases, the different layers of composite fibers 300 can be made from different materials, e.g., a first layer can be made from a first polymer and a second layer can be made from a second polymer. Having more than one layer may minimize or prevent tearing and other material-related failures of a heart valve leaflet.

In some cases, the exemplary fiber-reinforced composite material provided herein can include a layer of composite fibers 300 adjacent a solid, polymeric layer that does not contain fibers, e.g., a polymer film or coating. For instance, in some cases, an exemplary fiber-reinforced composite material provided herein can include a polymer film disposed over a plurality of composite fibers 300 or a layer of composite fibers 300.

Figure 4A:
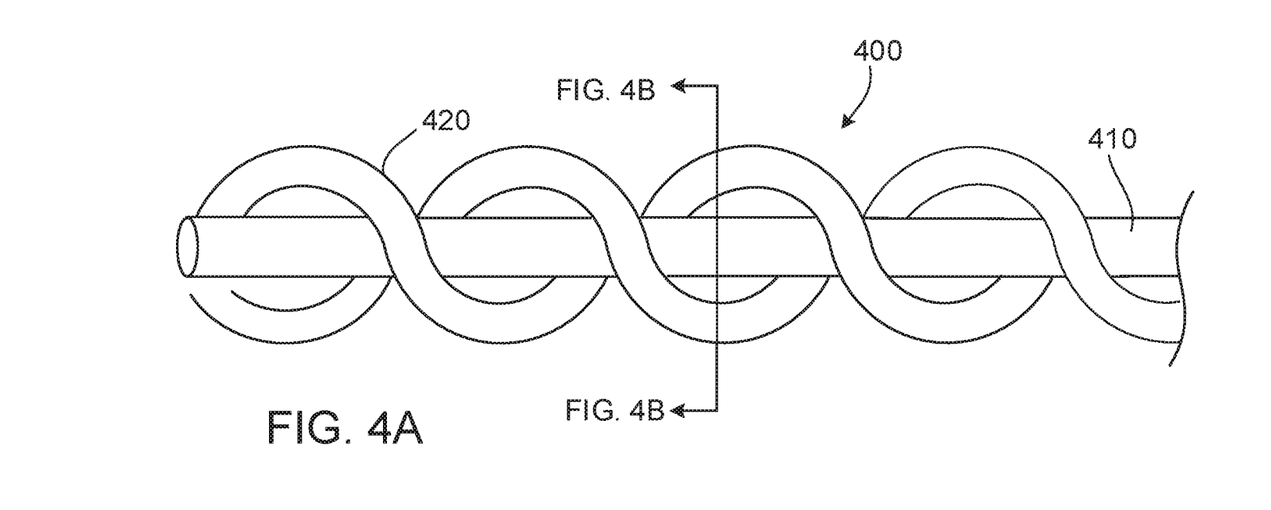
FIG. 4A provides a side perspective view of the composite fiber.
Figure 4B:
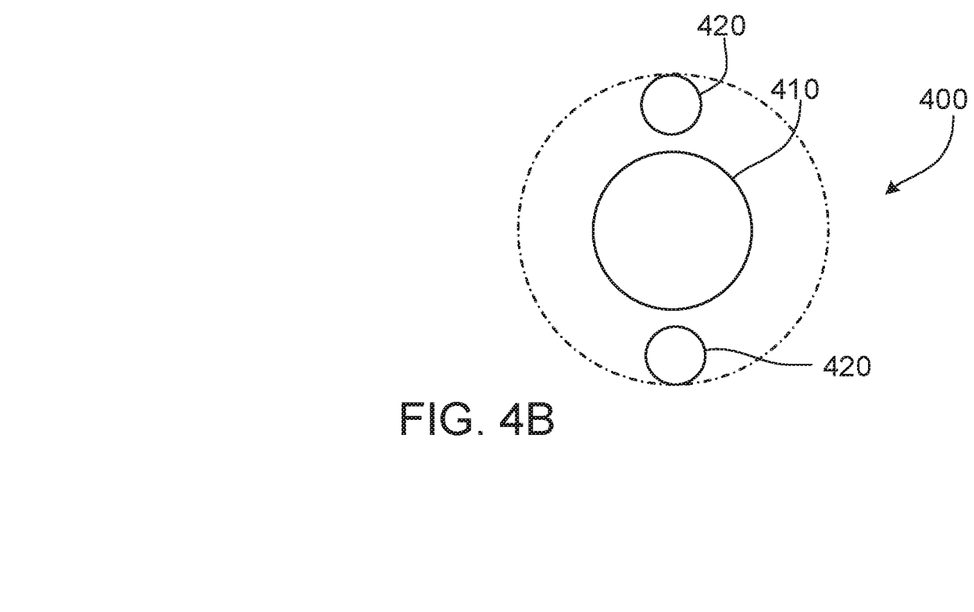
FIG. 4B provides a cross-sectional view of the composite fiber of FIG. 4A.

FIGS. 4A and 4B show another example of a composite fiber 400 provided herein. The composite fiber 400 includes a core fiber 410 and two sheathing fibers 420 disposed about the core fiber 410. The depicted sheathing fibers 420 can be spirally wrapped around the core fiber 410, in some cases. In some cases, features provided herein for the composite fiber 300 of FIG. 3 can also apply to the composite fiber 400.

A composite fiber 400 provided herein may include two, three, four, five, or more than five sheathing fibers 420 spirally disposed about a core fiber 410. In some cases, at least two or more sheathing fibers 420 can be spirally disposed about each other in addition to being spirally disposed about the core fiber 410.

Figure 5:
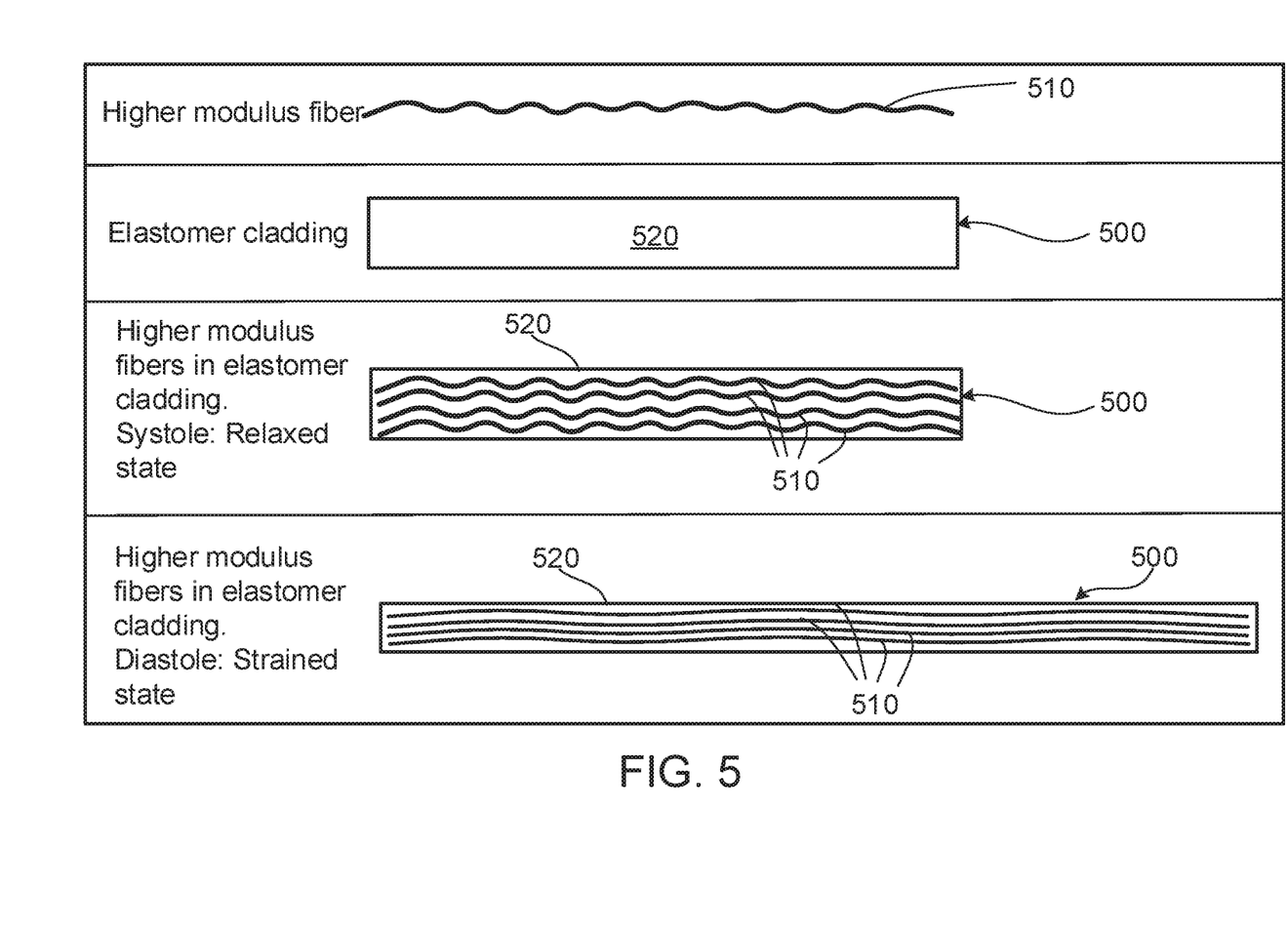
FIG. 5 provides schematic illustrations of another example of a composite fiber provided herein and components thereof.

FIG. 5 shows another example of a composite fiber 500 provided herein. The depicted composite fiber 500 includes multiple core fibers 510 encapsulated within a sheathing fiber 520. Each core fiber 510 can be encapsulated within the sheathing fiber 520 (e.g., an elastomeric sheathing fiber) such that each core fiber 510 has a non-linear shape when the composite fiber 500 is in a relaxed (non-stretched) state. In some cases, the non-linear shape of the core fiber 510 can include an undulating shape with respect to a longitudinal axis defined by the composite fiber 500. Each core fiber 510 can change to a linear (i.e., straight) shape within the sheathing fiber 520 when the composite fiber 500 is stretched out. In some cases, each composite fiber 500 can include only one core fiber 510 having an undulating form within a sheathing fiber 520. In some cases, the composite fiber 500 can have two, three, four, five, six or more than six undulating core fibers 510 within the sheathing fiber 520.

Figure 6A:
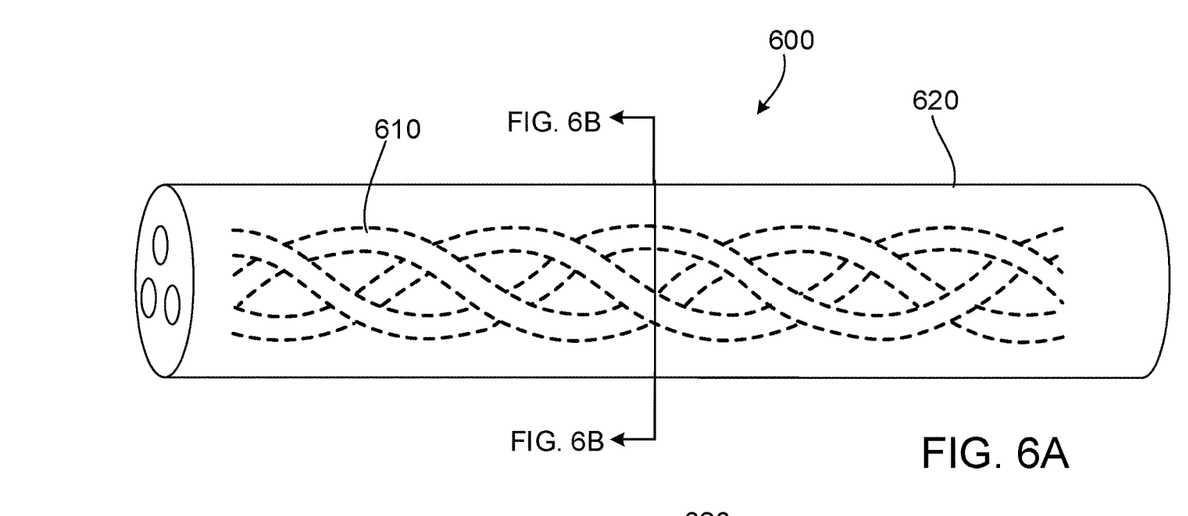
FIG. 6A provides a perspective view of the composite fiber showing core fibers within the composite fiber.
Figure 6B:
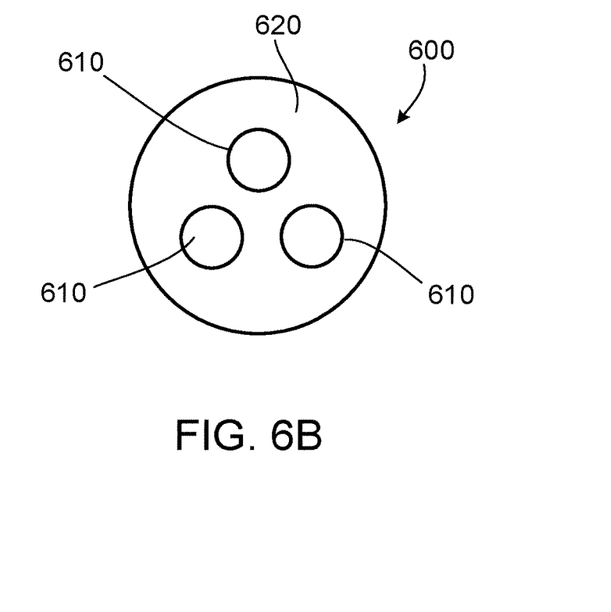
FIG. 6B provides a cross-sectional view of the composite fiber of FIG. 6A.

FIGS. 6A and 6B show another example of a composite fiber 600 provided herein. The depicted composite fiber 600 includes three core fibers 610 encapsulated within a sheathing fiber 620, e.g., an elastomeric sheathing fiber. The core fibers 610 of the depicted composite fiber 600 are helically disposed about a longitudinal axis of the composite fibers 600, forming a triple helix shape within the sheathing fiber 620.

Figure 7:
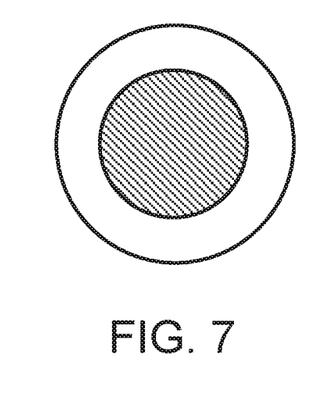
FIGS. 7-13 provide cross-sectional views of various exemplary composite fibers provided herein.
Figure 8:
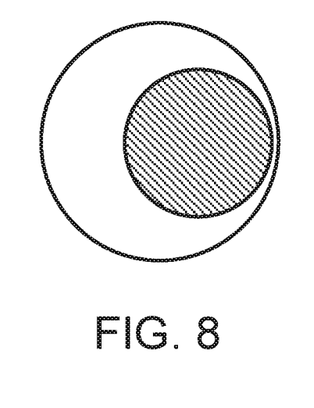
Figure 9:
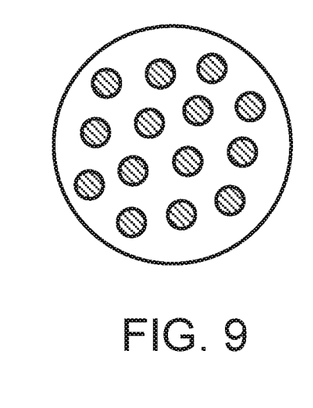
Figure 10:
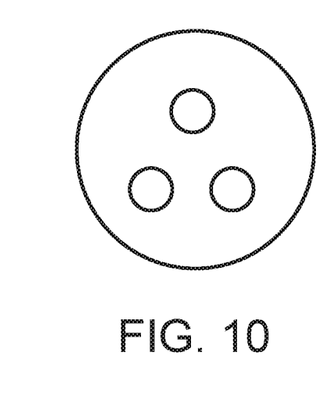
Figure 11:
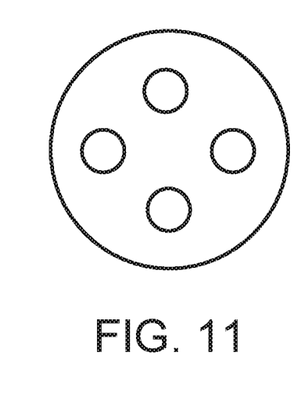
Figure 12:
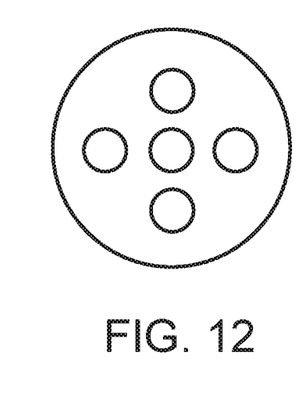
Figure 13:
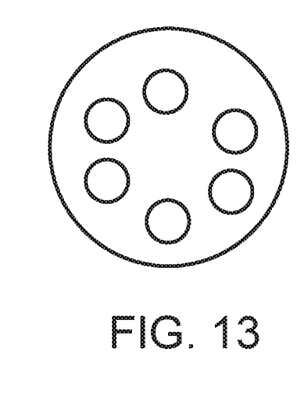

FIGS. 7-13 show cross-sectional views of various composite fibers provided herein. FIGS. 7 and 8 provide examples of a composite fiber having a single core fiber and encapsulated within a sheathing fiber. In FIG. 7, the core fiber is concentrically positioned within the sheathing fiber. In FIG. 8, the core fiber is off-center (i.e., non-concentric) with respect to the sheathing fiber. FIGS. 9-13 provide examples of composite fibers that include a plurality of core fibers encapsulated within a sheathing fiber. An exemplary composite fiber can include, but is not limited to, two core fibers, three core fibers, four core fibers, five core fibers, six core fibers, seven core fibers, eight core fibers, nine core fibers, ten core fibers, eleven core fibers, twelve core fibers, thirteen core fibers, fourteen core fibers, or more than fourteen core fibers within a sheathing fiber. In some cases, a composite fiber can include one or more central core fibers, for example, core fibers of FIGS. 9 and 12. In some cases, a composite fiber can include non-central core fibers, for example, core fibers of FIGS. 10, 11 and 13. In some cases, a core fiber can be disposed about one or more other core fibers. For example, one or more core fibers may be disposed spirally about a central core fiber.

Composite fibers provided herein can include a sheathing fiber that has been surface modified to provide desired surface characteristics. In some cases, the surface modification can include applying a coating of polyethylene glycol over the composite fiber.

The composite fiber provided herein can be made of various materials that include polymers, ceramics, and metals. In some cases, the core fiber or sheathing fiber is made of a polymer, such as a thermoplastic, a thermoset, or an elastomeric material. In some cases, the core and/or sheathing fibers can be made of a polymer having ceramic or metallic nanofibers, fillers, and/or particulates. The core fiber and the sheathing fiber(s) can be made of different materials to achieve a composite fiber having mechanical properties that are characteristic of two or more materials. In some cases, the material of the core fiber has a higher modulus than the material of the sheathing fiber. In some cases, the material of the core fiber has a lower modulus than the material of the sheathing fiber. In some cases, at least a portion of the core fiber and at least a portion of the sheathing fiber can optionally be made of the same or similar materials.

Composite fibers of the leaflets described herein can be made of various materials suitable for medical devices and/or implants. The composite fibers can be made of various biostable and/or biocompatible materials. A biostable material is a material that is resistant to degradation over a predetermined time period, e.g., 5 years, 10 years, 15 years, 20 years, or a time period equal to a use life of a medical device. A biocompatible material is a synthetic or natural material that is not harmful to living tissue. In general, fibers described herein can be composed of polymers, metals (e.g., titanium, stainless steel, tantalum), ceramics (fiberglass, acrylics), or combinations thereof. In some cases, fibers are made of thermoplastic polymers, thermoset polymers or combinations thereof. Fibers provided herein can be made of various polymeric materials, such as fluoropolymers, polyurethanes or block copolymers. Suitable polymers for fibers provided herein can be formed from fluoropolymers including, but not limited to, for example, polytetrafluoroethylene (PTFE), polyvinylidene fluoride (PVDF) (e.g. Kynar™ and Solef™), poly(vinylidene fluoride-co-hexafluoropropene) (PVDF-HFP) and combinations thereof. Other suitable fiber polymers can include urethane-based polymers such as polyurethanes, polyurethane elastomers (e.g. Pellethane), polyether-based polyurethanes (e.g. Tecothane), polycarbonate-based polyurethanes (e.g. Bionate and Chronoflex) and combinations thereof. In some cases, other examples of suitable polymer materials for fibers include, but are not limited to, polycarbonates, polyethers, polyesters such as polyethylene terephthalate (PET), polyethylenes, polypropylenes, polyamides (e.g., Kevlar®, Pebax®, nylon 6 and nylon 12), polyetheretherketones (PEEK), polysulfones, polyvinyl alcohols, polyetherimides, polyimide (PI), polybenoxazole (PBO), polybenzothiazole (PBT), polybenzimidazole (PBI), poly-N-phenylbenzimidazole (PPBI), polyphenylquinoxaline (PPG), poly(p-phenylene terephthalamide) (PPTA), polysulfone, naphtalate based polymer fibers such as polybuthylenenaphtalate (PBN) and polyethylenenaphtalate (PEN), polyhydroquinone-diimidazopyridine (PIPD or also known as M5 fibers) and combinations thereof. In some cases, fibers are formed from block copolymers such as, for example, a poly(styrene-isobutylene-styrene) (SIBS) triblock polymer and a polyisobutylene urethane copolymer (PIB-PUR).

In some cases, polyisobutylene urethane copolymers (PIB-PUR) can be used to form composite fibers provided herein. PIB-PUR is composed of soft segment portions and hard segment portions. Polyurethane hard segment portions can include, but are not limited to, methylene diphenyl diisocyanate (MDI), 4,4'-Methylene dicyclohexyl diisocyanate (H12MDI) and hexamethylene (HMDI). Polyurethane soft segment portions can include polyisobutylene macrodiol or polyisobutylene diamine. In some cases, suitable soft segments can include linear, branched or cyclic forms of polyalkene, polyether, a fluorinated polyether, a fluoropolymer, a polyester such as polyethylene terephthalate (PET), a polyacrylate, a polymethacrylate, a polysiloxane, a fluorinated polysiloxane, or a polycarbonate and derivatives thereof. PIB-PUR and PIB-PUR derivatives have the advantages of providing an inert, biocompatible, non-thrombobogenic and anti-calcifying material for medical devices and implants.

Composite fibers of the composite material of a leaflet can, in some cases, be made of a liquid crystalline polymer (LCP). LCPs are a special class of aromatic polyester or polyamide copolymers that have semi-crystalline properties due to regions of highly ordered crystalline structures formed therein. LCPs are materials that are generally chemically inert and have a high creep resistance, a high modulus and a high tensile strength. Suitable fiber materials made of LCPs include, but are not limited to, thermotropic polyesters such as poly(p-phenylene terephthalamide) (PPTA), poly (phenylene benzobisoxazole) (PBO), and combinations thereof. Other suitable LCPs can include poly(p-phenylene terephthalamide), such as Kevlar®, Vectran®, Poly(m-phenylene isophthalamide) such as Nomex® and Teijinconex®, Herachron®, Technora®, Twaron®, and Zylon®. In some cases, other high performance fibers can utilized, such as gel-spun ultra-high molecular weight polyethylene (Dyneema® and Spectra®). Benefits of using LCPs include providing leaflets with optionally thinner and smaller dimensions, e.g., thickness or diameter, without compromising mechanical properties of the leaflet, such as tensile strength, or performance characteristics such as robustness and durability. In some cases, diameters of composite fibers made of LCPs can be as small as 0.5 micrometers (or µm). In some cases, thicknesses of a leaflet composed of composite fibers made of LCPs can range from about 50 µm to about 100 µm.

The composite fibers and/or the polymer matrix of the fiber-reinforced composite material can be made of various biostable and/or biocompatible polymeric materials. In some cases, the polymer matrix can be made of a thermoplastic, thermoset, or an elastomeric polymer. Suitable polymer matrix materials can include, but are not limited to, homopolymers, copolymers and terpolymers. Various polyurethanes can be used to construct the polymer matrix, such as polyurethanes with soft segments such as polyether, perfluoropolyether, polycarbonate, polyisobutylene, polysiloxane, or combinations thereof.

In some cases, the composite fibers and/or polymer matrix of the fiber-reinforced composite material can be formed from block polymers such as, for example, poly(styrene-isobutylene-styrene) (SIBS) tri-block polymers. Other suitable elastomeric materials include, but are not limited to, silicones, nitrile rubber, fluoroelastomers, polyolephin elastomers, latex-type elastomers, various natural elastomers such as those made from collagen, elastin, cellulose, proteins, carbohydrates, and combinations thereof.

In some cases, individual composite fibers can be encapsulated within a jacket (e.g., a polymer jacket) to promote bonding between the composite fibers and a polymer matrix material.

The core fiber or sheathing fibers of the composite fibers provided herein, in some cases, can include fillers to form composite fibers to increase the tensile strength of the composite fibers. Suitable fillers can include, but are not limited to, carbon nano-sized tubes, ceramic fillers such as talc, calcium carbonate, mica, wollastonite, dolomite, glass fibers, boron fibers, carbon fibers, carbon blacks, pigments such as titanium dioxide, or mixtures thereof. The amount of filler included in the core fiber or sheathing fibers of the composite fibers provided herein may vary from about 0 wt % to about 20 wt % of the combined weight of fiber polymer and filler. Generally amounts from about 5 wt % to about 15 wt % and from about 0 wt % to about 4 wt %, may be included. In some cases, the core fiber or sheathing fibers of the composite fibers provided herein contain less than 1 wt % by weight filler and are substantially free of fillers.

Composite fiber density, such as fiber weight percent, within a composite material can vary. In some cases, weight percent of composite fibers within a fiber-reinforced composite material can generally range from about 0.1 wt % to about 50 wt %, including all ranges and values therebetween. In some cases, for example, the fiber weight percentage can range from 0.1 to 0.5 wt %, 0.5 to 1 wt %, 1 to 2 wt %, 2 to 3 wt %, 3 to 4 wt %, 4 to 5 wt %, 5 to 10 wt %, 10 to 20 wt %, 20 to 30 wt %, 30 to 50 wt %, 0.5 to 30 wt %, 1 to 20 wt %, 2 to 10 wt %, or 3 to 5 wt %. In some cases, the fiber weight percentage of a composite material can range from about 1 wt % to about 5 wt %. The fiber weight percentage can significantly affect physical and/or mechanical properties of a composite material. In some cases, a suitable fiber weight percentage can be used to customize or adjust the physical and/or mechanical properties of a leaflet material.

Although the prosthetic heart valves provided herein are generally made of synthetic materials, such as materials made of composite fibers, in some cases, prosthetic heart valves can be made of both synthetic materials and non-synthetic materials such as mammalian tissue (e.g., porcine or bovine tissue). For example, in some cases, at least a portion of a leaflet provided herein can be made from composite fibers provided herein as well as tissue obtained from an animal, e.g., bovine pericardium or porcine tissue.

Figure 14:
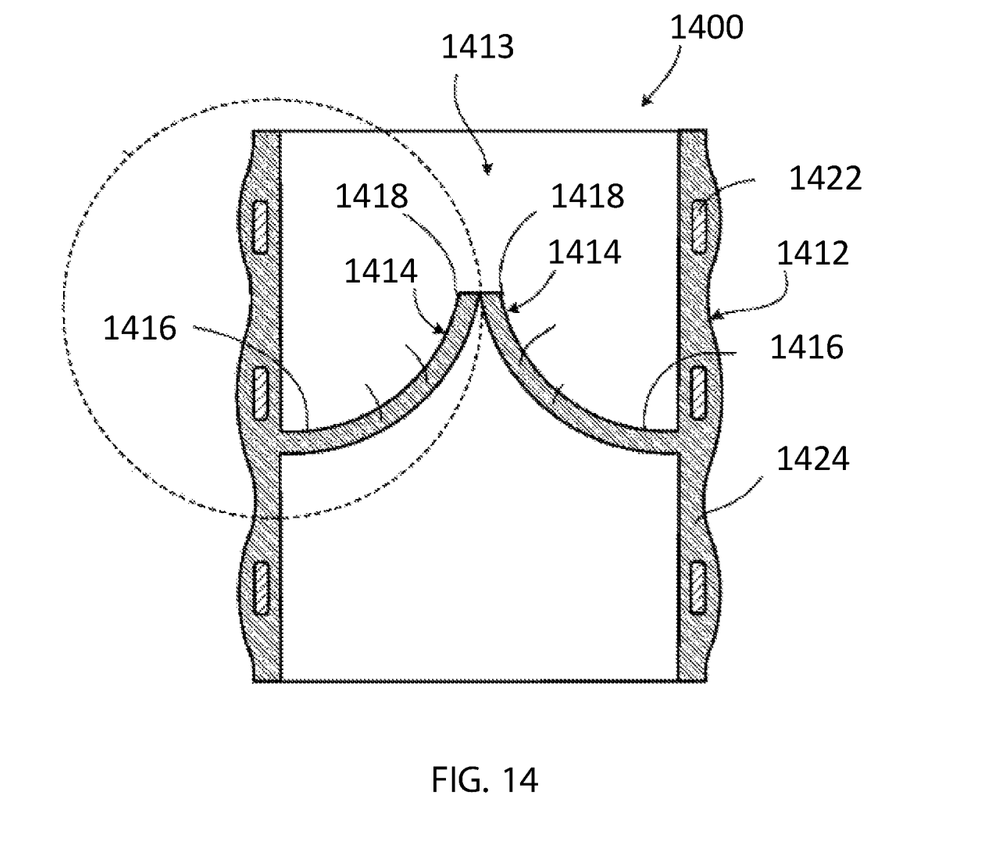
FIG. 14 is an illustration of another exemplary prosthetic heart valve provided herein.

FIG. 14 provides another embodiment of a prosthetic heart valve 1400. Prosthetic heart valve 1400 includes a base 1412 defining a substantially cylindrical passage 1413 and a plurality of polymeric leaflets 1414 disposed along the substantially cylindrical passage 1413. Each polymeric leaflet 1414 includes a respective root portion 1416 coupled to base 1412 and a respective edge portion 1418 movable relative to the root portion 1416 to coapt with the edge portions of the other polymeric leaflets along a coaptation region. In some cases, the entire heart valve 1400 can be made of a fiber-reinforced composite material provided herein. In some cases, portions of heart valve 1400, e.g., the polymeric leaflets 1414 of the heart valve 1400, can be made of a fiber-reinforced composite material provided herein. In some cases, the polymeric leaflets 1414 can include a plurality of composite fibers provided herein.

Base 1412 includes a frame 1422 disposed in a polymer layer 1424. The polymer layer 1424 can be composed of fiber-reinforced composite materials provided herein. In some cases, polymer layer 1424 can include a plurality of composite fibers 1414 provided herein. Polymer layer 1424 secures respective root portions 1416 of polymeric leaflets 1414 to the base 1412. Polymer layer 1424 can form a substantially continuous surface with respective root portions 1416 of polymeric leaflets 1414. This can reduce the likelihood of stress concentrations at the junction of respective root portions 1416 and base 1412. Additionally or alternatively, polymer layer 1424 can be disposed between each of polymeric leaflets 1414 and frame 1422 such that polymer layer 1424 protects polymeric leaflets 1414 from inadvertent contact with frame 1422 (e.g., as can occur through eccentric deformation of prosthetic heart valve 1400 on a calcium deposit present at the implantation site).

In some cases, frame 1422 is substantially cylindrical such that the outer surface of the base 1412 is substantially cylindrical and the polymer layer 1424 disposed on the frame 1422 forms the substantially cylindrical passage 1413. In some cases, frame 1422 is completely disposed in the polymer layer 1424, with the polymer layer 1424 forming a contoured outer surface of the valve 1400. In some cases, the frame 1422 is partially disposed in the polymer layer 1424. In some cases, the polymer layer 1424 is applied to the frame 1422 to form a substantially smooth inner and/or outer surface of the valve 1400.

Methods of Forming Composite Fibers

Various methods can be applied when forming composite fibers provided herein. In some cases, electrospinning can be used to form the core fiber and/or the sheathing fiber of the composite fiber. Suitable methods for forming at least a portion of the composite fibers include, but are not limited to, compression molding, extrusion, solvent casting, injection molding, force spinning, melt-blowing, and combinations thereof. Examples of other methods for partially or fully constructing a part composed of a composite material also include, but are not limited to, dip coating, roll coating, spray coating, flow coating, electrostatic spraying, plasma spraying, spin coating, curtain coating, silkscreen coating, and combinations thereof. In some cases, the processes described herein can be used to form composite fibers and/or a polymer matrix of a fiber-reinforced composite material.

In some cases, the core fibers and the sheathing fibers are constructed simultaneously. In some cases, the core fibers and the sheathing fibers of the core are constructed separately. In the latter case, the sheathing fibers can be disposed about the core fiber(s) and then subjected to a bonding process, which will be discussed later in further detail.

Polymer fibers (e.g., nanofibers) can be generated, in some cases, through combining a template method with an extrusion process. In this process, polymer fibers can be formed when molten polymer is forced through pores of an anodic aluminum membrane and cooled thereafter. In a subsequent process, a sheathing fiber(s) can be disposed about a core fiber by wrapping or braiding one or more polymer fibers around the core fiber. In some cases, wrapping or braiding can be achieved by using an electrospinning process or, in the case of a more complex braid involving multiple sheathing fibers, with a braiding equipment capable of mechanically wrapping or braiding fibers.

An elastomer sheathing fiber can be formed, in some cases, by forming a first elastomeric layer, depositing core fibers configured with an undulating form on the first elastomeric layer, and adding a second elastomeric layer over the core fibers. The fibers can be encapsulated within the sheathing fiber by adding the second elastomeric layer. In some cases, core fibers can be pre-formed and inserted into a mold or extruder that injects a sheathing material around the core fibers.

Various bonding processes can be used to bond the core fiber(s) and the sheathing fiber(s) together. In some cases, the core and sheathing fibers can be bonded together by a corona discharge exposure. In some cases, either the core or the sheathing fibers can be melted to facilitate bonding between the core and sheathing fibers. Adhesive bonding can also be used to providing bonding between the core and sheathing fibers, in some cases.

Composite fibers provided herein can include surface modifying the core and/or sheathing fibers to provide desired surface characteristics. In some cases, surface modification can include plasma treatment. In some cases, surface modification includes adding a coating to an exterior surface of the core and/or sheathing fibers. In some cases, a polymer coating can be applying to exterior surfaces of the composite fibers using one of many types of applications. Suitable coating applications can include, but are not limited to, dip and spray coating processes.

In some cases, an exemplary method of forming a prosthetic heart valve material can include disposing one or more layers composed of composite fibers using one or more of the processes provided herein.

We claim:

1. A prosthetic heart valve leaflet comprising a fiber-reinforced structure including a plurality of composite fibers, each composite fiber comprising a plurality of elastomeric core fibers encapsulated within a common sheathing fiber disposed about the plurality of elastomeric core fibers, wherein the common sheathing fiber fills a space between the plurality of elastomeric core fibers such that they do not touch one another;
wherein each elastomeric core fiber in the plurality of elastomeric core fibers has an undulating, non-linear shape within the common sheathing fiber when the composite fiber is in a relaxed state, and a straight, linear shape within the common sheathing fiber when the composite fiber is stretched in a strained state.

2. The prosthetic heart valve leaflet of claim 1, wherein weight ratio of the elastomeric core fibers to the sheathing fiber ranges from 1:5 to 5:1.

3. The prosthetic heart valve leaflet of claim 1, wherein the elastomeric core fibers and the sheathing fiber are made of different polymeric materials.

4. The prosthetic heart valve leaflet of claim 1, wherein the sheathing fiber comprises a thermoplastic polymer.

5. The prosthetic heart valve leaflet of claim 1, wherein the elastomeric core fibers comprise a tensile modulus that is greater than a tensile modulus of the sheathing fiber.

6. The prosthetic heart valve leaflet of claim 1, wherein the elastomeric core fibers or the sheathing fiber comprises carbon fillers.

7. The prosthetic heart valve leaflet of claim 1, wherein the composite fiber includes a coating comprising polyethylene glycol.

8. The prosthetic heart valve leaflet of claim 1, wherein the composite fibers are electrospun composite fibers.

9. The prosthetic heart valve leaflet of claim 1, each composite fiber comprising at least three elastomeric core fibers encapsulated within the sheathing fiber.

10. The prosthetic heart valve leaflet of claim 9, wherein the at least three elastomeric core fibers form a helical shape within the sheathing fiber.

* * * * *